United States Patent [19]

Bicer

[11] Patent Number: 5,061,278
[45] Date of Patent: Oct. 29, 1991

[54] ARTIFICIAL HEART VALVE

[76] Inventor: Demetrio Bicer, 4 Oakdale St., Irvine, Calif. 92714

[21] Appl. No.: 557,159

[22] Filed: Jul. 23, 1990

[51] Int. Cl.$^5$ .............................................. A61F 2/24
[52] U.S. Cl. .................................... 623/2; 137/512.1; 137/527
[58] Field of Search ................. 623/2; 137/512.1, 527, 137/527.8

[56] References Cited

U.S. PATENT DOCUMENTS

| | | | |
|---|---|---|---|
| 3,546,711 | 12/1970 | Bokros | 623/2 |
| 4,078,268 | 3/1978 | Possis | 623/2 |
| 4,494,253 | 1/1985 | Bicer | 623/2 |
| 4,863,459 | 9/1989 | Olin | 623/2 |

OTHER PUBLICATIONS

Demetrio Bicer, "Criteria for Selecting a Heart Valve Prosthesis", Publishes Circa 1987, pp. 1-21.

Primary Examiner—Ronald Frinks
Attorney, Agent, or Firm—Price, Gess & Ubell

[57] ABSTRACT

A prosthetic heart valve of the type that includes an annular support ring and at least one valving member. The valving member includes a pair of rotational members and the annular support ring includes a pair of apertures that each support a releasable insert. The releasable inserts include axle members that have a predefined rotational contact surface and the rotational members include depressions having a predefined rotational support surface. The geometries of the rotational contact surface and rotational support surfaces are such that a substantial point contact of rotation exists when the two surfaces are rotationally engaged. The invention may be conversely practiced with the releasable inserts including a depression and the rotational members including axle members.

22 Claims, 2 Drawing Sheets

ARTIFICIAL HEART VALVE

BACKGROUND OF THE INVENTION

1. Field of the Invention

The present invention relates generally to prosthetic devices and, more specifically, to a new heart valve prosthetic and bearing assembly therefor.

2. Description of Related Art

Prosthetic heart valves are mechanical valve devices that are implanted in a patient in order to replace a damaged or diseased natural tissue valve. In general, the known heart valve prostheses are comprised of an annular support member and at least one valving member operatively supported by the annular support member in order to provide a one-way flow of blood therethrough. The annular support member generally carries a suture ring on its exterior for attachment to the existing heart tissue.

As might be imagined, the replacement of a patient's heart valves with prosthetic heart valves places heavy demands, not only on the patient and the surgeon, but also on the designer of the prosthetic heart valves themselves. Designers are primarily concerned with patient compatibility and durability.

With regard to compatibility, heart valve prostheses must have exceptional hemodynamic (blood flow) characteristics that are comparable to that of a healthy, natural valve. Specific hemodynamic criteria might include minimization of pressure gradients on either side of an open valve; minimization or prevention of hemolysis, the destruction of red blood cells; minimization of stenosis, a narrowing of the valve opening that results in decreased blood flow; minimization of regurgitation or backward flow of blood through the valve; and minimization of turbulence that might provide resistance to smooth laminar blood flow.

Hemolysis, the destruction of red blood cells, is typically caused by crushing the red blood cells between parts of the valve during the opening and closing operation, and sometimes caused by shearing forces exerted on the cells as they rapidly pass by rough valve components such as worn parts or cloth. The crushed red cells that result from hemolysis may result in the formation of emboli or thromboli. Emboli are abnormal particles that circulate in the blood, whereas thromboli are abnormal particles that form a blood clot at a fixed position within a blood vessel. The minimization of hemolysis is paramount because the thrombus may break off, move through the patient's circulatory system and occlude a blood vessel, and thereby cause serious damage to organs, stroke, paralysis, and even death. If the thrombus resides near the prosthetic heart valve, it may result in the patient's death by growing large enough to cause valve thrombosis (i.e., forcing the valves to remain either open or closed). Valve thrombosis is frequently a sudden and catastrophic event.

Prosthetic heart valves, constituting foreign matter to the patient's body, tend to encourage thrombus formation. Because of this tendency, it is important to construct valve components from smooth and chemically inert materials. Moreover, the valve design must nearly eliminate crushing contact between moving valve parts.

Durability is as equally paramount as good hemodynamic characteristics, because an implanted heart valve prosthetic may open and close some 50,000,000 times each year. Durability is clearly parameter where such heavy demands are made on a device in which the patient's life lies in balance. Once a heart valve prosthetic has been implanted in a patient, it is unlikely that the heart valve will ever be replaced or repaired. In general, open heart surgery to replace or repair an existing heart valve prosthetic is riskier than leaving it in and living with the odds that it could fail.

Durability might be defined as a prosthetic heart valve's ability to withstand physical and chemical stresses produced within the heart. The goal of the designer is to avoid the necessity of reoperation and the possibility of gradual or catastrophic heart valve failure. In general, valves must be able to withstand large and rapid pressure changes, mechanical stress created by continuous opening and closing, and resistance to gradual change in physical and/or structural properties that may produce deterioration. Durability is affected by the material selected and the valve design. The best patient-compatible materials are thromboresistant and have a very low density. Unfortunately, such materials typically have very low resistance to mechanical stresses and exhibit high frictional characteristics.

DELRIN, the trade name for one manufacturer's polymer, is a good thromboresistant material, but has poor frictional and wear characteristics. Carbon/pyrolite, like DELRIN, is also a good patient-compatible material, but may be subject to fatigue damage at points of movement. At the other end of the spectrum, stainless steel alloys have good physical wear and frictional properties, but their high density and weight result in a prosthetic heart valve that requires an excessive amount of energy to open and close.

The known heart valve prostheses may be subdivided into a finite number of general valve types, all offering various advantages and disadvantages.

The known heart valves prostheses include: tissue valves; free-floating disc valves (FIG. 7A); ball and cage valves (FIG. 7B); pivoting disc valves (FIG. 7C); bi-leaflet valves (FIG. 7D); and the Bjork-Shiley valve (FIG. 7E). The free-floating disc valve and the ball and cage valve are generally considered undesirable because of the pressure gradients that develop on opposite sides of the open valve, and because the valve member (the disc or the ball) obstruct the blood flow and severely diminish the hemodynamics of the valves. The Bjork-Shiley valve was introduced in the late 1970s but was recalled because the two metal struts that control the movement of the disc were prone to stress and potential catastrophic breakage.

The present inventor is of the opinion that the pivoting disk and/or bi-leaflet disc valves, or variations thereof, are the best known choice of valve design for making a compromise between patient compatibility, good hemodynamics, and excellent durability. In general, pivoting leaflet valves are comprised of an annular support member, at least one valving member, and bearing means on opposite sides of the valving members to allow rotation of the valving members relative to the annular support member. In general, such bearing means is comprised of an axle member that protrudes outwardly from the valving member and a corresponding concave support surface that extends inwardly into the annular support member or, conversely, a valving member that extends inwardly from the annular support member and a corresponding convex support surface that extends inwardly into the valving member.

As might be imagined, the weak link in the durability characteristics of pivoting leaflet valves is the junction between the protruding axle member and the corresponding concave support surface. The axle member and the supporting concave surface physically contact one another, and because of continuous opening and closing, are subject to repetitive stress and frictional forces. For durability purposes, this application requires materials, such as stainless steel, having good frictional and wear characteristics. However, as mentioned above, the valve material must also be patient-compatible. In addition to being durable, it must have good thromboresistant characteristics and must not be so dense that excessive energy must be expended in opening and closing the valve. The problem is that there is no known material that possesses both patient-compatible characteristics and desirable physical characteristics.

The known pivoting leaflet prosthetic heart valves are typically comprised of carbon/pyrolite components. Carbon/pyrolite is generally considered the best compromise material for today's technology because it is relatively light, wear resistant, exhibits good frictional characteristics, and is thromboresistant. Unfortunately, carbon/pyrolite is brittle because it is manufactured by being externally hardened under high heat. Carbon/pyrolite is therefore subject to stress fractures at the rotational points of contact between the axle member and corresponding concave support surface.

In addition, the known pivoting leaflet heart valves having annular support rings and leaflets are assembled by compressing the annular support member on opposite sides and perpendicular to the rotational axis of the leaflets. The inward assertion of pressure at the described location deforms the annular support member and causes the concave support surface to expand outward just enough to allow the axle members of the leaflet to be inserted therebetween. Once the pressure is released, the concave support surfaces return to their original position to enclose the axle members of the pivoting leaflet.

The problem with the above method of installation, necessitated by the unitary carbon/pyrolite structure of the known prosthetic heart valve components, is that fatigue is introduced into the crystalline structure of the annular support member. This fatigue is very undesirable in prosthetic heart valves because it is possible that failure may later result therefrom. In addition, this type of prosthetic heart valve requires that an outer metallic ring be placed around the carbon/pyrolite annular support member in order to ensure that the annular support member does not fatally release the leaflets by expanding after implantation. Because the metallic retaining ring must be extremely rigid and relatively large, it must be detrimentally made of a material that typically is not thromboresistant. For example, the retaining ring is generally made from titanium. Moreover, the added metallic retaining ring necessarily reduces the Effective Orifice Area (EOA) of the valve because the outer dimensions of the total structure are limited by the anatomy of the patient.

U.S. Pat. No. 4,078,268, issued to Zinon on Mar. 14, 1978, discloses a bi-leaflet heart valve prosthetic, one embodiment of which includes a bearing insert threaded into the annular support member. The Zinon device, however, suffers from several infirmities. In particular, prior to reaching the threaded bearing plug, the axle member protruding from the leaflet must extend through and rotate within a cylindrical aperture provided in the annular support member. In addition to the frictional contact between the axle member and the wall of the cylindrical aperture, the Zinon device encourages thrombosis by crushing or tearing red blood cells in the space defined between these two rotating surfaces. Extreme clotting in this space may even prevent the valve from opening and closing altogether. Another problem with the Zinon device is that there is full surface contact, rather than point contact, between the bearing insert and the axle member, resulting in unnecessary friction and further exacerbating the possibility of thrombosis. Finally, the disclosed method of retaining the bearing insert in the annular support member is a threaded joint, which joint may loosen during use with disastrous life-threatening consequences.

SUMMARY OF THE INVENTION

It is an object of the present invention to solve the above-described problems associated with the prior art heart valves.

In particular, it an object of the present invention to provide an improved heart valve wherein only the load bearing portions of the heart valve need be comprised of materials having desirable physical characteristics such that a majority of the heart valve may be comprised of a patient-compatible material;

It is a further object of the present invention to provide a heart valve wherein the valving members may be easily installed in the annular support member and without need for flexing the annular support member or the valving members during assembly and further such that the annular support members may be beneficially made of a relatively rigid inflexible material;

It is a further object of the present invention to provide a heart valve that does not require an exterior metallic retaining ring such that the Effective Orifice Area (EOA) of the valve may be beneficially increased;

It is a further object of the present invention to provide a heart valve wherein the axle member need not protrude through an aperture to reach the rotational support surface such that red blood cells are not crushed by the rotation of the axle member within the aperture, and It is a further object of the present invention to provide a heart valve having little physical contact between the axle members and the rotation support surfaces such that minimal rotational friction is present and such that minimal red blood cells are crushed during valving operation.

An improved heart valve according to the present invention is comprised of a bearing system for use with a heart valve prosthesis of the type having a support member that includes an outside wall and an inside annular wall through which blood may flow and having at least one valving member that includes first and second opposed axle members having rotation contact surfaces that are pivotally connected to opposite sides of said inside annular wall, the improvement comprising: first and second apertures extending between the outside wall and the inside annular wall of said support member; first and second bearing inserts located respectively within said first and second apertures, said bearing inserts having a rotation support surface exposed on said inside annular wall when installed therein, said rotation contact surfaces and said rotation support surfaces defining a point contact of rotation therebetween; and retaining means for retaining said bearing inserts within said apertures.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 5 is a graphical representation of the contact surfaces of FIGS. 3 and 4a;

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a new bearing assembly for use with prosthetic devices.

Figure 1:
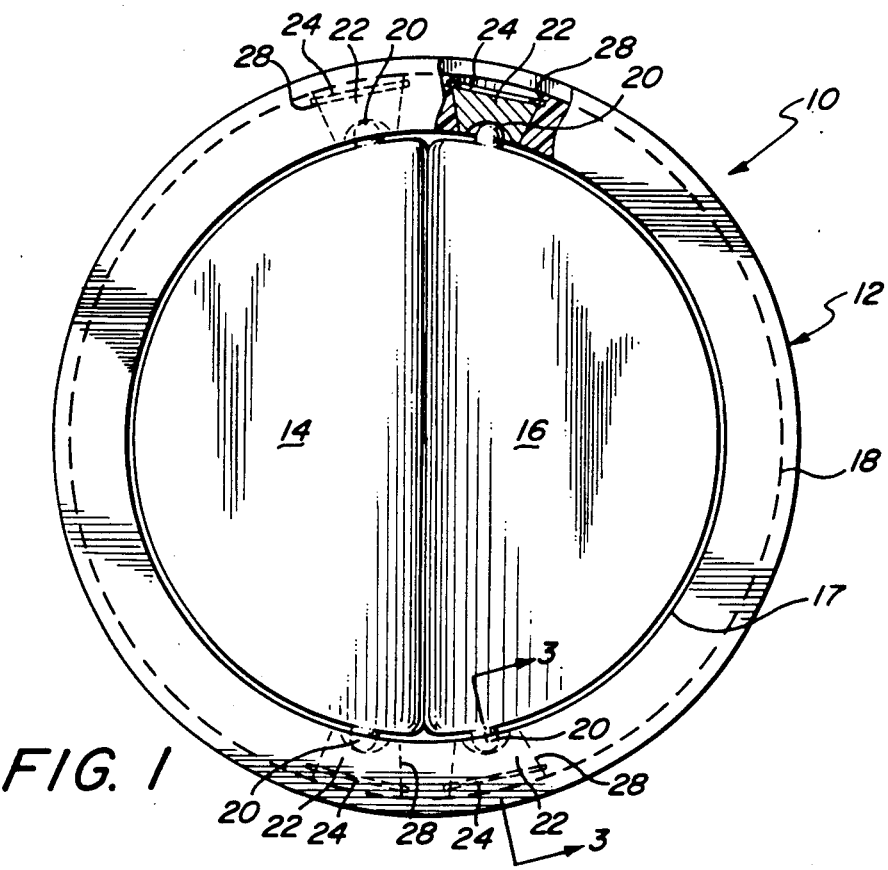
FIG. 1 is an elevational view of a bi-leaflet heart valve according to the present invention.
Figure 2:
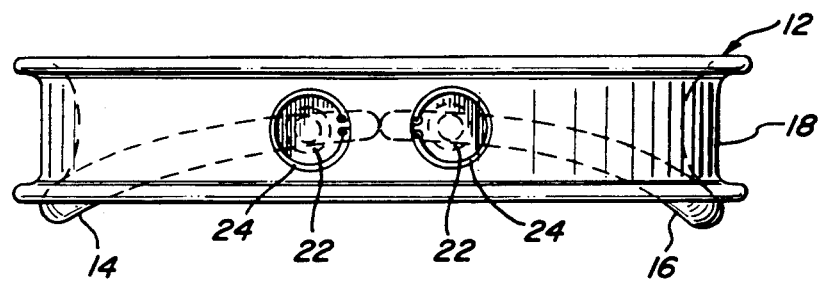
FIG. 2 is a top pan view of the bi-leaflet heart valve of FIG. 1.

FIG. 1 is an elevational view of a preferred bi-leaflet prosthetic heart valve 10 according to the present invention. As shown, heart valve 10 is comprised of an annular support member 12 that includes an inside annular wall 17 through which blood may flow and an outside annular groove 18 in which a suture ring (not shown) may be attached. The annular support member 12 further includes two pairs of frustoconical apertures 28 which extend from the outside annular groove 18 to the inside annular wall 17.

A pair of leaflets 14, 16 or valving members are disposed in the aperture designed by the inside annular wall 17. Each valving member 14, 16 includes a pair of axle members 20 which extend from said valving members 14, 16 at opposite ends thereof.

Two pairs of bearing inserts 22 are disposed in the frustoconical apertures 28 of the annular support member 12. In the preferred embodiment, the apertures 28 and the bearing inserts 22 are frustoconical in shape so that the bearing inserts 22 will naturally seat in the apertures 28.

An important feature of the present invention is the minimization of contacts between the axle members 20 and the support surfaces of the bearing inserts 22. A point contact of rotation therebetween minimizes friction and reduces the possibility of crushed blood cells.

Figure 3:
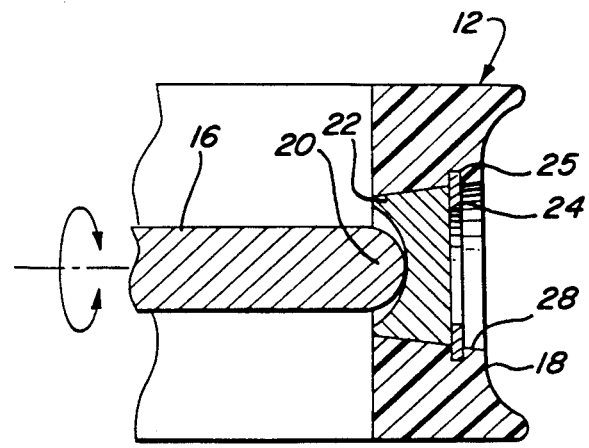
FIG. 3 is a cross-sectional view taken along lines 3—3 of FIG. 1 showing a preferred releasable heart valve bearing according to the present invention.
Figure 4A:
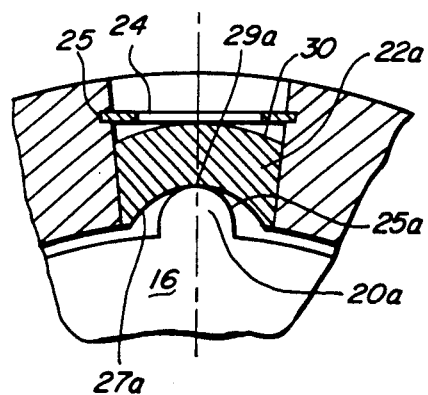
FIGS. 4a and 4B are cross-sectional views taken along lines 4—4 of FIG. 2 showing first and second preferred releasable heart valve bearings according to the present invention.
Figure 4B:
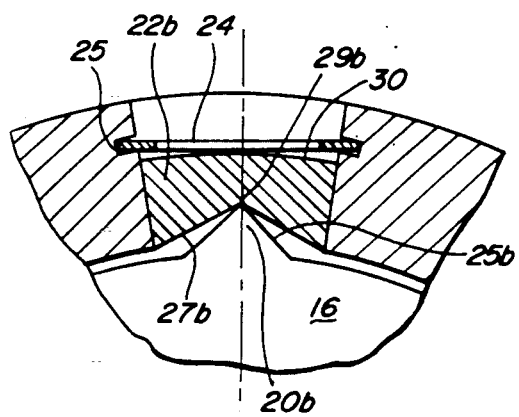

Thus, in the preferred embodiment, the working geometries of the rotation surfaces 25a and 25b and the corresponding support surfaces 27a, 27b are such that a point contact of rotation is defined therebetween. FIGS. 3, 4a, and 4b depict two alternative rotation geometries. In FIGS. 4a and 4b, it can be seen that the axle members 20 respectively include a rotation surface 25a, 25b, and that the bearing inserts 22 include a corresponding support surface 27a, 27b.

Figure 5:
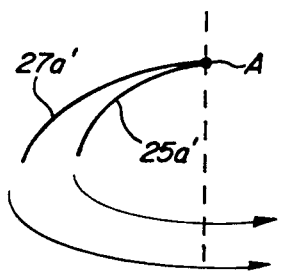

Referring specifically to FIG. 4a, axle member 20a has a convex curved rotation surface 25a, and bearing insert 22a has a concave curved support surface 27a. The relative curvatures of the rotation surface 25a and the support surface 27a are such that a point contact of rotation occurs therebetween. This can be best seen or understood by referring to FIG. 5, which graphically depicts curved lines 25a' and 27a', which have a common tangent point of intersection A relative to the plane contained in point A that is normal to the axis of rotation.

Figure 6:
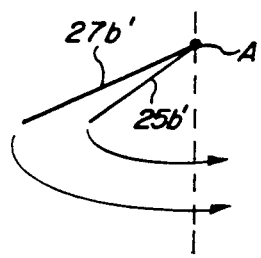
FIG. 6 is a graphical representation of the point contact surface of FIG. 4B.
Figure 7A:
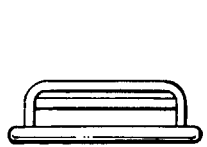
FIGS. 7a through 7e depict various prior art heart valves.
Figure 7B:
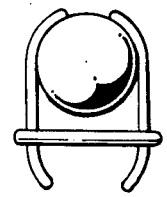
Figure 7C:
Figure 7D:
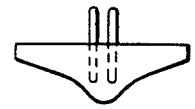
Figure 7E:

FIG. 4b depicts an alternative embodiment of the present invention wherein axle member 20b includes a conical rotation surface 25b, and bearing insert 22b includes a corresponding conical support surface 27b. FIG. 6 is a graphical representation of lines 25b' and 27b' that may be rotated about a common axis of rotation to mathematically define rotation surface 25b and support surface 27b. As with the curved rotational and support surfaces defined or depicted in FIG. 4a, the conical surfaces depicted in FIG. 4b result in a point contact of rotation.

The conical surfaces 25b, 27b result in a point contact of rotation that naturally stays in one axial location. The curved surfaces 25a, 27a, also resulting in a point contact of rotation, may have some tendency to float relative to one another.

As already described, it is important that prosthetic heart valve components be constructed from material that is patient-compatible; in other words, material that is light and chemically inert. Because such materials generally do not exhibit good frictional or wear characteristics, the production of a heart valve prosthetic where the annular support member 12 and the valving members 14, 16 are made of such materials results in a prosthetic device of poor durability. However, in accordance with the present invention, the majority of the heart valve prosthetic 10 may be constructed of such patient-compatible materials, yet the portions of the heart valve prosthetic 10 subject to friction and wear may be made of materials better suited for durability purposes.

In the preferred embodiment, the annular support member 12 and the valving members 14, 16 are made of carbon/pyrolite, a material that has proven to be suitable for prosthetic purposes. Other known patient-compatible materials are, of course, equally suitable. The preferred material for use as bearing inserts 22 possesses strength and very low frictional qualities. Note that the present invention allows for the use of hard inflexible materials to comprise the annular support member 12 and the valving members 14, 16. Such materials include titanium, exhibiting very good physical and compatibility characteristics. The bearing inserts 22 may, for instance, be constructed of titanium or a carbide such as diamond or ruby.

The preferred method of retaining bearing inserts 22 within apertures 28 is the provision of an annular groove 25 that extends axially around the inside wall of each aperture 28. After the insert 22 is seated on an aperture 28 below the annular groove 25, a compressible split ring member 24 may be compressed and allowed to expand into the annular groove 25 so as to retain the bearing insert. As shown in FIGS. 4a and 4b, the upper surface 30 of the bearing inserts 22a or 22b may have a convex curvature so that the split ring retaining clip 24 positively bears on surface 30 to bias the bearing inserts 22a or 22b into the aperture 28. In an alternative embodiment, the upper surface 30 may be flat, whereas the split ring 24 has a curvature.

The bearing inserts according to the present invention have an inwardly directed end face to be positioned adjacent the inside annular wall provided with a depression having a rotation support surface 27a or 27b that is fully exposed on the inside annular wall 17 of the annular support member 12 since no portion of the annular wall overlies the inwardly directed end surface. Thus, the axle members 20 need not protrude through a cylindrical aperture provided on the inside annular wall 17 in order to reach a support surface and red blood cells are not crushed by rotation of axle members 20 within a cylindrical aperture.

Figure 8:
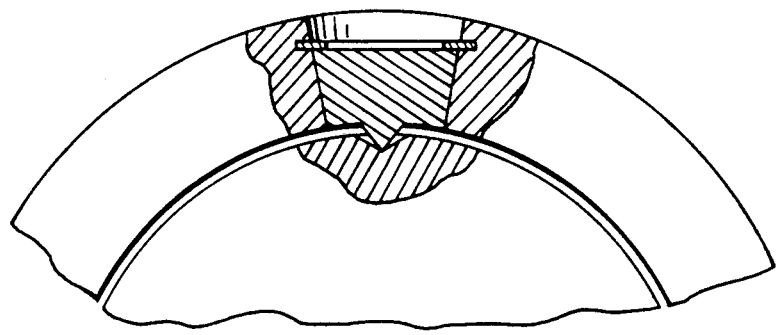
FIG. 8 is a partial cross-sectional view of an alternative embodiment of a releasable heart valve bearing according to the present invention.

A prosthetic heart valve incorporating the bearing inserts according to the present invention is relatively simple and cost effective to assemble compared to the known heart valves. For example, a first of two bearing inserts 22a associated with one valving member 16 is installed in the aperture 28. One of the rotational members 20a of the valving member 16 is then simply positioned against the rotational support surface 27a of the bearing insert 22a. The other of the two bearing inserts 22a is then inserted in another aperture 28 to engage the other rotational member 20 on the opposite side of the valving member 16. This method of installation beneficially allows maintenance of the end play tolerances necessary for proper heart valve operation and durability Other embodiments are, of course, possible. For example, the present invention could be practiced with a single valving member or, as shown in FIG. 8, the axle members could be carried by inserts whereas the bearing members could reside on opposite sides of the valving members. In addition, other geometries resulting in the disclosed point contact of rotation may be possible.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved bearing system for use with a heart valve prosthesis of the type having a support member that includes an outside wall and an inside annular wall through which blood may flow and having at least one valving member that includes first and second rotation contact surfaces that are pivotally connected at opposite sides of said inside annular wall, the improvement comprising:
   first and second apertures extending between the outside wall and the inside annular wall of said support member;
   first and second bearing inserts located respectively within said first and second apertures, said bearing inserts having a rotation support surface exposed on said inside annular wall when installed therein, said rotation contact surfaces and said rotation support surfaces defining a point contact of rotation therebetween; and
   retaining means for retaining said bearing inserts within said apertures.

2. The improved bearing system of claim 1 wherein said rotation contact surfaces and said rotation support surfaces are defined by rotating a curved line about an axis of rotation, the curvature of said rotation contact surface being less than the curvature of said rotation support surface such that a floating point contact of rotation results therebetween.

3. The improved bearing system of claim 1 wherein said rotation contact surfaces and said rotation support surfaces are defined by rotating a straight line about an axis of rotation, the angle between the axis of rotation and the straight line defining said rotation contact surface being less than the angle between the axis of rotation and the straight line defining said rotation support surface such that a fixed point contact of rotation results therebetween.

4. The improved bearing system of claim 1 wherein said retaining means is comprised of the surface of said bearing inserts and the surface of said apertures being respectively in the shape of the frustrum of a right circular cone such that said bearing insert seats in said aperture.

5. The improved bearing system of claim 4 wherein said retaining means is further comprised of:
   an annular groove on the inside wall of said apertures, said bearing insert being located below said annular groove when seated in said aperture; and
   a split ring retaining clip that fits within said annular groove and retains said bearing insert within said aperture.

6. The improved bearing system of claim 5 wherein said split ring retaining clip is curved such that said split ring retaining clip biases said bearing insert into said aperture.

7. The improved bearing system of claim 1 wherein said first and second bearing inserts are comprised of a carbide selected from the group consisting of ruby and diamond.

8. The improved bearing system of claim 1 wherein said first and second bearing inserts are comprised of titanium.

9. An improved bearing system for use with a heart valve prosthesis of the type having a support member that includes an outside wall and an inside annular wall through which blood may flow and having at least one valving member, the improvement comprising:
   first and second apertures extending between the outside wall and the inside annular wall of said support member;
   first and second inserts located respectively within said first and second apertures;
   first and second rotation members provided on said valving member, said first and second members rotationally engaging said first and second inserts, respectively, to comprise a pair of rotational junctions between which said valving member may rotate, and
   one of said insert and said respective rotation member of each rotational junction being comprised of an axle member having a rotation contact surface and the other being comprised of a depression having a rotation support surface, said one insert having an inwardly directed end face adjacent said inside annular wall with no portion of said inside annular wall overlying said end face, whereby said rotation support surface. is fully exposed to said rotation contact surface of said axle member such that said axle member need not protrude through an aperture to reach said rotation support surface and red blood cells are not crushed by rotation of said axle member within said aperture.

10. The improved bearing system of claim 9 further comprising:
retaining means for retaining said inserts within said apertures.

11. The improved bearing system of claim 9 wherein said rotation contact surface and said rotation support surface define a point contact of rotation therebetween.

12. The improved bearing system of claim 9 wherein said first and second inserts are comprised of a carbide selected from the group consisting of ruby and diamond.

13. The improved bearing system of claim 9 wherein said first and second inserts are comprised of titanium.

14. The improved bearing system of claim 11 wherein said rotation contact surfaces and said rotation support surfaces are defined by rotating a curved line about an axis of rotation, the curvature of said rotation contact surface being less than the curvature of said rotation support surface such that a floating point contact of rotation results therebetween.

15. The improved bearing system of claim 11 wherein said rotation contact surfaces and said rotation support surfaces are defined by rotating a straight line about an axis of rotation, the angle between the axis of rotation and the straight line defining said rotation contact surface being less than the angle between the axis of rotation and the straight line defining said rotation support surface such that a fixed point contact of rotation results therebetween.

16. An improved bearing system for use with a heart valve prosthesis of the type having a support member that includes an outside wall and an inside annular wall through which blood may flow, and having at least one valving member, the improvement comprising:
first and second apertures extending between the outside wall and the inside annular wall of said support member;
first and second bearing inserts located respectively within said first and second apertures; and
a pair of rotational junctions made integral with the bearing inserts and valving member enabling said valving member rotation, said rotational junctions comprising an axle member having a rotation contact surface and a depression having a rotation support surface, said rotation contact surface and said rotation support surface defining a point contact of rotation therebetween.

17. The improved bearing system of claim 16 wherein the valving member includes first and second axle members having rotation contact surfaces and said bearing inserts have depressions defining rotation support surfaces exposed on said inside annular wall.

18. The improved bearing system of claim 17 wherein said rotation contact surfaces and said rotation support surfaces are defined by rotating a curved line about an axis of rotation, the curvature of said rotation contact surfaces being less than the curvature of said rotation support surfaces such that a floating point contact of rotation results therebetween.

19. The improved bearing system of claim 17 wherein said rotation contact surfaces and said rotation support surfaces are defined by rotating a straight line about an axis of rotation, the angle between the axis of rotation and the straight line defining rotation contact surface being less than the angle defined between the axis of rotation and the straight line defining said rotation support surface such that a fixed point contact of rotation results therebetween.

20. The improved bearing system of claim 16 wherein the bearing inserts include axle members extending inward from said inside annular wall and said valving member includes depressions defining rotation support surfaces.

21. The improved bearing system of claim 20 wherein said rotation contact surfaces and said rotation support surfaces are defined by rotating a curved line about an axis of rotation, the curvature of said rotation contact surfaces being less than the curvature of said rotation support surfaces such that a floating point contact of rotation results therebetween.

22. The improved bearing system of claim 20 wherein said rotation contact surfaces and said rotation support surfaces are defined by rotating a straight line about an axis of rotation, the angle between the axis of rotation and the straight line defining rotation contact surface being less than the angle defined between the axis of rotation and the straight line defining said rotation support surface such that a fixed point contact of rotation results therebetween.

* * * * *